United States Patent
Rathjen et al.

(10) Patent No.: US 9,603,743 B2
(45) Date of Patent: Mar. 28, 2017

(54) DEVICE FOR PROCESSING MATERIAL OF A WORKPIECE AND METHOD FOR CALIBRATING SUCH A DEVICE

(75) Inventors: Christian Rathjen, Bremen (DE); Holger Lubatschowski, Gehrden (DE); Tammo Ripken, Wunstorf (DE)

(73) Assignee: ROWIAK GMBH, Hannover (DE)

( * ) Notice: Subject to any disclaimer, the term of this patent is extended or adjusted under 35 U.S.C. 154(b) by 878 days.

(21) Appl. No.: 13/995,771

(22) PCT Filed: Dec. 22, 2011

(86) PCT No.: PCT/EP2011/006529
§ 371 (c)(1),
(2), (4) Date: Jun. 19, 2013

(87) PCT Pub. No.: WO2012/084255
PCT Pub. Date: Jun. 28, 2012

(65) Prior Publication Data
US 2013/0274725 A1 Oct. 17, 2013

(30) Foreign Application Priority Data

Dec. 23, 2010 (DE) .......................... 10 2010 055 966

(51) Int. Cl.
*A61B 18/18* (2006.01)
*A61F 9/008* (2006.01)
(Continued)

(52) U.S. Cl.
CPC ...... *A61F 9/00806* (2013.01); *A61F 9/00825* (2013.01); *A61B 8/10* (2013.01);
(Continued)

(58) Field of Classification Search
CPC .............. A61F 9/00825; A61F 9/00806; A61F 2009/00855; A61F 2009/00851;
(Continued)

(56) References Cited

U.S. PATENT DOCUMENTS 6,786,899 B1 * 9/2004 Lai .......................... A61B 3/113
606/10
6,817,998 B2 * 11/2004 LaHaye ................. A61B 18/20
606/10

(Continued)

FOREIGN PATENT DOCUMENTS

DE    10 2006 046 370 A1    4/2008
DE    10 2006 053 119 A1    5/2008
(Continued)

OTHER PUBLICATIONS

Form PCT/IB/338 Notification of Transmittal of Translation of the International Preliminary Report on Patentability date of mailing Jul. 4, 2013 (1 page).

(Continued)

*Primary Examiner* — Timothy J Neal
(74) *Attorney, Agent, or Firm* — Flynn, Thiel, Boutell & Tanis, P.C.

(57) ABSTRACT

A device for processing material of a workpiece, the device including a pulsed processing laser, a focusing lens, a beam-deflection unit, a control unit and a confocal detector unit. The intensity of the laser radiation is variable. An imaging unit is provided to detect structures within the workpiece using electromagnetic radiation, wherein the electromagnetic radiation of the imaging unit is radiated via the beam-deflection unit and the focusing lens into the workpiece, and evaluating device is provided and compares the position of the focus of the laser radiation determined by the detector unit with the expected position of the focus in the image of the workpiece obtained by the imaging unit.

13 Claims, 1 Drawing Sheet

(51) Int. Cl.
*A61B 18/04* (2006.01)
*A61B 8/10* (2006.01)

(52) U.S. Cl.
CPC ............... *A61F 2009/00851* (2013.01); *A61F 2009/00855* (2013.01)

(58) Field of Classification Search
CPC ...... A61F 9/008; A61F 9/00838; A61F 9/009; A61B 8/10
USPC .......................................... 606/5, 6
See application file for complete search history.

(56) References Cited

U.S. PATENT DOCUMENTS

| | | | |
|---|---|---|---|
| 7,863,543 | B2 | 1/2011 | Bischoff et al. |
| 2006/0106371 | A1* | 5/2006 | Muhlhoff ................ A61F 9/008 606/5 |
| 2008/0078752 | A1 | 4/2008 | Bischoff et al. |
| 2008/0319428 | A1 | 12/2008 | Wiechmann et al. |
| 2009/0137993 | A1 | 5/2009 | Kurtz |
| 2010/0082017 | A1 | 4/2010 | Zickler et al. |
| 2010/0324543 | A1 | 12/2010 | Kurtz et al. |
| 2011/0102810 | A1 | 5/2011 | Bischoff et al. |
| 2011/0118712 | A1 | 5/2011 | Lubatschowski et al. |
| 2012/0016352 | A1 | 1/2012 | Dick et al. |

FOREIGN PATENT DOCUMENTS

| | | |
|---|---|---|
| DE | 10 2008 005 053 A1 | 7/2009 |
| DE | 11 2008 002 511 T5 | 7/2010 |
| DE | 10 2009 012 873 A1 | 9/2010 |
| WO | WO 2008/112292 A1 | 9/2008 |
| WO | WO 2010/075571 A2 | 7/2010 |

OTHER PUBLICATIONS

Form PCT/IB/373 Translation of International Preliminary Report on Patentability dated Jun. 25, 2013 (1 page).
Form PCT/ISA/237 Translation of Written Opinion of the International Searching Authority (7 pages).
Office Action of European Patent Office issued in European Application No. 11 804 651.5 dated Dec. 2, 2013 (6 pages).
Form PCT/ISA/210 International Search Report dated Mar. 14, 2012 (4 pages).
Office Action of German Patent Office issued in German Application No. 10 2010 055 966.0 dated Nov. 23, 2011 (6 pages).

* cited by examiner

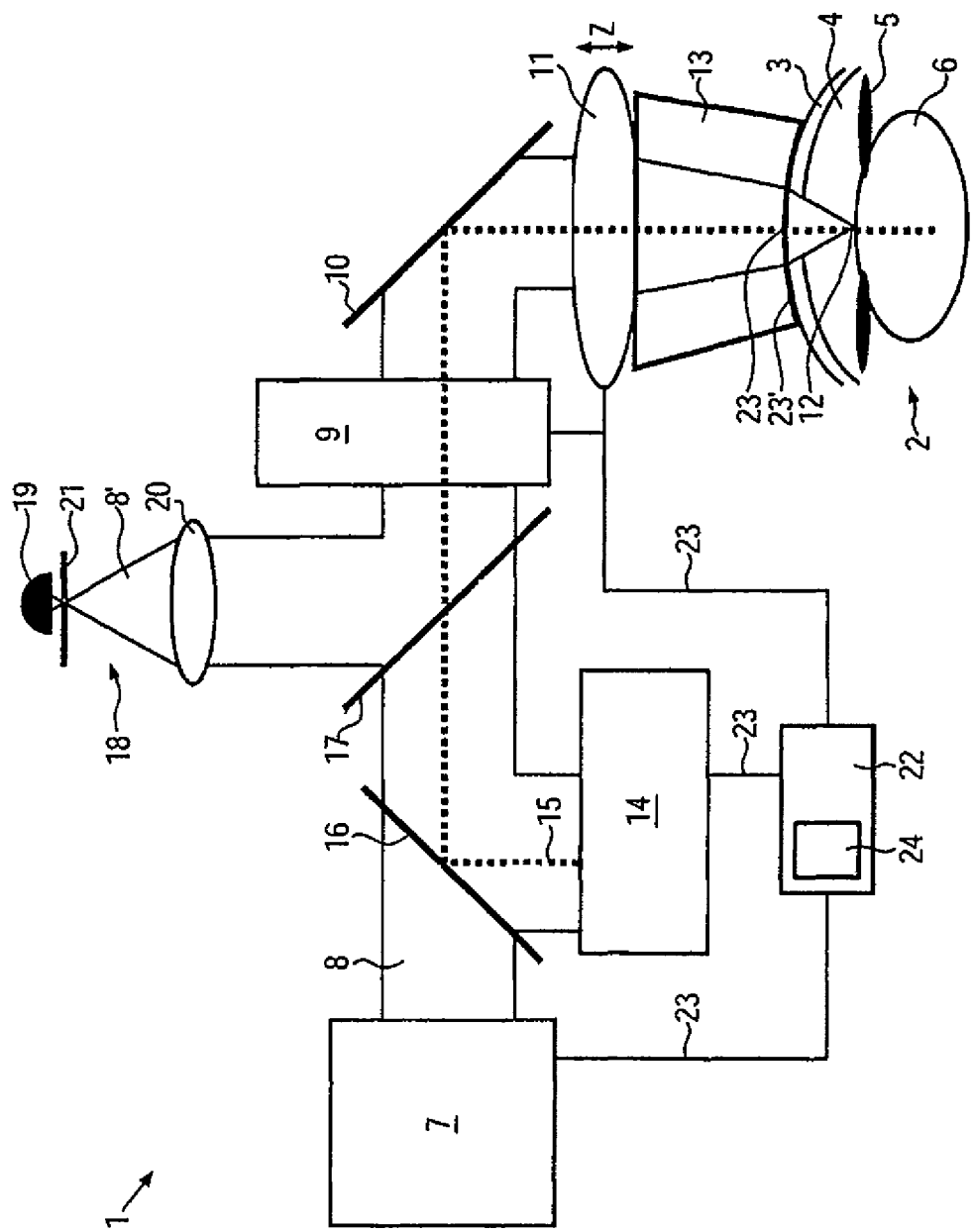

DEVICE FOR PROCESSING MATERIAL OF A WORKPIECE AND METHOD FOR CALIBRATING SUCH A DEVICE

The present invention relates to a device for processing material of a workpiece according to the preamble of claim 1, as well as to a method for calibrating a device for processing material.

A device for processing material according to the preamble of claim 1 is disclosed in DE 10 2006 046 370 A1. The device for processing material described therein is in particular used for correcting defective vision using laser eye surgery. With this laser eye surgery, in particular with the so-called femtosecond Lasik, an eye of a patient is sucked and fixed onto a contact glass. Subsequently, pulsed radiation of a femtosecond laser is focused in the interior of the cornea of the eye to achieve optical breakdown therein. At the location of the optical breakdown, the material is cut. Scanning the laser focus creates a tapestry of a series of optical breakdowns. At this cut, the cornea can be opened in order to remove, for example, a lenticule cut by the same technique from the interior of the cornea. In this manner, the shape of the cornea and thereby the refractive properties of the eye can be changed to improve the vision of the patient.

Having the most precise knowledge of the location of the focus in the workpiece, in this case the cornea of the eye, is important in this method. Deviations of the focal position lead to a changed sectional geometry, which can significantly worsen the treatment outcome.

To improve the precision of the beam guidance, DE 10 2006 046 370 A1 proposes reducing the intensity of the laser radiation until it is no longer sufficient for generating an optical breakdown at the point of focus of the laser radiation. Consequently, the laser can irradiate into the eye without treating it. The focus of the laser is then guided along a predetermined path through the eye already being docked onto the contact glass, for example along a circular or spiral path. The radiation reflected from the respective location of the focus of the laser radiation into the path of the working laser beam is measured using a confocal detection unit. At the boundaries between the eye and the contact glass, the reflection is particularly strong due to the refractive index step there. At the points with particularly high reflection, the predetermined path of the focus of the laser radiation therefore intersects the boundary between the eye and the contact glass. If a majority of such cutting points was determined, with knowledge of the shape of the contact glass, a conclusion regarding the position of the workpiece under the contact glass can be drawn. This method thereby allows calibration of the beam shaping unit of the processing laser to the position of the contact glass.

Another method for correcting the focus position of a treatment laser in the surgical correction of defective vision of an eye is disclosed in DE 10 2006 053 119 A1. This method is intended to consider, during the laser treatment, not only the position of the cornea of the eye at the contact glass, but also the deformation of the cornea of the eye, in order to place the foci of the processing laser radiation at the desired locations The correction proposed for this is performed by a relatively complex computational method.

It is particularly disadvantageous with the method known from DE 10 2006 046 370 A1, that for controlling the position of the laser focus, only the boundary between the eye and a contact glass is considered. This method results in errors when deeper structures in the eye or in other workpieces are to be processed and the distance between the location of processing and the surface of the sample thereby increases. The known method is not suitable for example for laser correction of vision defects of the eye's natural lens, which is described for example in DE 10 2008 005 053 A1. In addition, the method known from DE 10 2006 046 370 A1 cannot be applied if no contact glass is present.

DE 11 2008 002 511 T5 describes an ophthalmological laser system for cataract surgery. In order to pinpoint the surgical laser as precisely as possible, an OCT imaging module is integrated into the laser system. DE 10 2009 012 873 A1 describes an ophthalmological laser system for a different surgical procedure, namely for producing cuts in an eye lens or in the cornea of an eye.

The object of the present invention is to provide a device and a method for processing material enabling very exact pinpoint processing of the workpiece using devices that have a design as simple as possible.

This object is satisfied by a device having the features of claim 1 and by a method having the features of claim 9. Advantageous developments of the invention are disclosed in the dependent claims.

In contrast to the conventional processing devices, the device according to the invention for processing material of a workpiece comprises an imaging unit. This imaging unit is adapted to examine the workpiece and to detect in particular structures in the bulk of the workpiece. These structures can be functional and optically distinguishable components of the workpiece. When the workpiece is a human eye, the detected structures can, for example, be the eye lens, the anterior chamber, the cornea of the eye, or other components of the eye. The imaging unit has the advantage of being able to examine the workpiece with high spatial resolution already prior to processing. In this manner, the subsequent processing of the material can be prepared. In addition, the imaging unit provides the advantage of monitoring, documenting, and possibly correcting the processing of material during operation of the device.

However, the invention reaches beyond the use of an imaging unit for processing material, because it takes into account that physical reasons or not entirely accurate alignment of the imaging unit with the radiation path of the processing laser can lead to deviations between the expected and the actually present location of the focus of the laser radiation in the workpiece. To minimize or even eliminate these deviations, an evaluation unit is provided according to the invention and set up to compare the position of the focus of the laser radiation, determined by the confocal detector unit, with the expected position of the focus in the image of the workpiece obtained by the imaging unit. The positional difference of the actual and the expected focus can be determined from this comparison and respectively taken into account when processing the workpiece. This considerably increases precision for processing the workpiece. The detector unit is preferably a confocal detector unit. Alternatively, for example, the second order harmonic generation could also be used for detection.

In this, the device according to the invention has the advantage that no contact glass must be provided, so that undesired deformation of the workpiece caused by the contact glass is avoided. In contrast to prior art, the device according to the invention enables calibration or matching of the coordinate systems of the processing system and the imaging unit also in the deeper layers of the workpiece, not only at its surface. In this manner, errors can be avoided, which in prior art result from the deviation between the point of calibration (i.e., at the surface of the workpiece) and the point of processing (in the interior of the workpiece). Across this distance, for example, optical deviations can arise, which with conventional calibration techniques lead to a deviation of the coordinate systems at the point of processing—for example, a temperature drift, which is hard to control with conventional methods. With the device according to the invention, such errors are avoided so that processing precision is further increased. Another advantage of the method according to the invention is that the OCT no longer needs to also detect the contact glass. One can set the measuring range of the OCT to the target area. The OCT is now permitted to drift. A further advantage of the method arises for lenses which can no longer focus to the contact glass. Systems with such lenses can basically not use the prior art methods.

It can be particularly advantageous when the electromagnetic radiation of the imaging unit differs in its wavelength from the laser radiation of the processing laser. Because in this manner, the radiation of the imaging unit can substantially without loss be superimposed with the processing laser radiation (for example, using dichroic mirrors) and the optimum wavelength for processing and for imaging can be used. In this, the device according to the invention provides the advantage that, in contrast to conventional techniques, no dispersion-induced deviations of the coordinate systems of the imaging and processing result, in particular when using different wavelengths.

As explained above, with the device according to the invention, the actual location of the focus of the processing laser radiation can be correlated or calibrated with a reference point in the imaging system—and even if this reference point is located not only at the surface but in the bulk or interior of the workpiece. With conventional systems with calibration only at the boundary between the workpiece and the contact glass, however, the dispersion in the workpiece could lead to a deviation between the expected and the actual location of the focus of the processing laser radiation. This problem was increased in complex workpieces such as human eyes. The positional deviations could be computationally partly subtracted out by considering a dispersion curve of the material of the workpiece. However, uncertainties in the dispersion curve, individual peculiarities in the composition of the material of the workpiece (e.g. implants or retinal surgery with replacement fluids in the eyeball) or measurement errors and technical shortcomings (e.g., incomplete temperature compensation) nevertheless lead to a significant error between the intended and the actual focal position of the processing laser. This error is avoided with the device according to the invention by matching the focus position of the laser in the interior of the workpiece to the imaging unit.

The imaging unit is preferably a unit for optical coherence tomography, in short, an OCT unit. It is suitable to measure and characterize the workpiece with high spatial resolution. The spatial resolution can for example be from 1 to 10 microns. For example, an ultrasound imaging unit would in the alternative also be conceivable. Preferably, the control unit is configured to automatically correct the position of the focus of the laser radiation while considering a deviation of the determined position of the focus from the expected position of the focus. Alternatively thereto, the coordinate system of the imaging unit can be shifted in order to match the two coordinate systems of the imaging unit and the processing unit. It is also conceivable that an operator receives a proposal on a display for a correction or calibration of coordinate systems, which can then be confirmed by the operator.

In an advantageous embodiment, a dichroic beam splitter is provided for coupling the electromagnetic radiation of the imaging unit in the radiation path of the laser radiation of the processing laser. This dichroic beam splitter can be used when the processing laser radiation differs in its wavelength from the wavelength of the electromagnetic radiation of the imaging unit using the dichroic beam splitter, the two radiations can be brought to match almost without loss and be jointly directed onto the workpiece.

Preferably, a beam splitter is provided for uncoupling the laser radiation to the confocal detector unit, uncoupling at least 70% of the laser radiation to the confocal detector unit, preferably even 80% to 92%, ideally 90%. This has the disadvantage that a portion of the same size of the processing laser radiation is lost. However, this disadvantage can easily be compensated in that the output of the processing laser is increased accordingly. This is opposed by the tremendous advantage of a high light output to the confocal detector resulting in precise measurement with a high signal-to-noise ratio (SNR).

In an advantageous embodiment, the confocal detector unit comprises an aperture, an optical fiber and/or a detector having a relatively small detector surface, for example with dimensions of 100 microns or less. The aperture, the input of the optical fiber or the detector are in the focus of a lens that focuses the radiation from a particular target area in which the confocal measurement is taken. The aperture, the optical fiber or the detector each allow only light of that predetermined target volume to pass.

The invention also relates to a method for calibrating a device for processing material of a workpiece having the features of claim 9. In the method according to the invention, for calibration, the average output power of the processing laser is first reduced compared to the processing output. For example, the average output power is reduced to 30% to 50% of the "breakdown power" at which there occurs an optical breakdown in the material of the workpiece. In this manner, it is ensured that the reduced output power of the processing laser effects no changes in the material. It would be alternatively conceivable to focus the processing laser in a weaker manner to in this way reduce the intensity at the focus. However, this variant could be at the expense of resolution.

With reduced output power or intensity, the processing laser is focused at different depths in the interior of the workpiece. At the same time, at a fixed depth z (for a given lateral position x, y), a confocal measurement of the processing laser radiation reflected from there is taken in the interior of the workpiece. When the processing laser is focused to the location of the confocal measurement, the signal of the confocal measurement at certain points reaches a peak. These peaks occur at points where there is a jump (or step) in the refractive index in the workpiece, i.e. where two different material regions are contiguous. The method according to the invention records at which setting of the focusing lens the peaks in the confocal detection were determined for the processing laser. Simultaneously or subsequently, there is a comparison with the image of the workpiece which was captured by the imaging unit. The refractive index steps can be determined also in this image. Calibration of the imaging unit for matching the determined depth of the focus of the processing laser for the peaks of the confocal signal is effected in relation to a reference point located in the interior of the workpiece and thus in the immediate vicinity of the actual processing area. In this manner, subsequent processing of the material is very precise.

Preferably, the steps of focusing the processing laser radiation at reduced intensity, the confocal detection, determining the depth of focus and calibrating the imaging are performed at (or actually under) a plurality of surface points on the workpiece. In this manner, distortions in the representation by the imaging unit can be taken into account and compensated.

It is advantageous if calibration of the imaging unit is dynamic in dependency on the respective location of the focus of the processing laser in the workpiece. In this manner, local properties of the workpiece can be taken into account when matching the coordinate systems.

It is conceivable to match not only the imaging unit to the focal depth of the processing laser radiation, but also to collimate the position of the focus of the laser radiation while considering a deviation of the determined position of the focus from the expected location of the focus. For this purpose, the focusing lens for the processing laser can be adjusted accordingly.

For imaging, optical coherence tomography (OCT) of the workpiece can advantageously be performed.

It has already been explained that the work piece can in particular be a human eye. The device according to the invention and the method according to the invention are particularly advantageously used in preparation for subsequent processing of the lens of the eye or the retina.

In the following, an advantageous embodiment of the invention is further illustrated by means of a drawing.

FIG. 1 shows a schematic view of a device according to the invention for processing material of a workpiece.

The device shown schematically in FIG. 1 is used for processing a workpiece 2. In the present embodiment, the workpiece 2 is a human eye. The cornea 3, the anterior chamber 4, the iris 5, and the lens of the eye 6 are schematically illustrated.

The device 1 for processing material comprises a processing laser 7. This processing laser 7 generates laser radiation 8 in the form of short or ultrashort laser pulses. The processing laser 7 can in particular be a femtosecond laser.

The laser radiation passes through a beam-forming lens (or lens assembly) 9. In the beam-forming lens 9, the laser radiation can for example be expanded, in order to subsequently receive a particularly small focus. In addition, the beam profile of the laser radiation 8 can be smoothed or otherwise modulated.

The laser radiation 8 also passes through a deflection unit 10, which is an adjustable galvanically driven mirror or an x-y pair of such deflection mirrors. The deflection unit 10 serves changing the position of the focus of the laser radiation 8. Together, the beam forming lens and the deflection unit 9 form a beam-forming and beam deflection unit.

Furthermore, the laser radiation 8 passes through a focusing optic device 11, such as a focusing lens or a focusing lens system, of which only one focusing lens is shown in FIG. 1. The focusing lens 11 focuses the laser radiation 8 of the processing laser 7 to a focus 12 in the interior of the workpiece 2. In the schematically illustrated embodiment, the focus 12 is located on the front side of the eye lens 6. However, it can also be positioned in other locations in the bulk of the workpiece 2, in particular, inside the eye lens 6.

Between the focusing lens 11 and the eye 2, a patient interface is present, in the embodiment formed as a contact glass 13 onto which the cornea 2 of the eye 3 is docked. The contact glass 13 is transparent to the laser radiation 8, and it does not affect the quality of the laser radiation 8. The patient interface for example also comprises suction rings.

The device 1 for processing material further comprises an imaging unit 14—in the preferred embodiment, an OCT unit. The imaging unit 14 transmits electromagnetic radiation—in the case of an OCT unit, this is laser radiation 15. A dotted line schematically illustrates the radiation path of the electromagnetic radiation 15.

A dichroic mirror 16 being located in the radiation path of the laser radiation 8 of the processing laser 7 transmits the laser radiation 8 but is highly reflective to the electromagnetic radiation 15 of the OCT unit 14. The dichroic mirror 16 is oriented such that it couples the electromagnetic radiation 15 of the OCT unit 14 in a collimated manner in the radiation path of the processing laser radiation 8. Consequently, the radiation 15 of the OCT unit 14, in the same manner as the processing laser radiation 8, passes through the beam forming lens 9, the deflection unit 10 and the focusing lens 11 before it enters into the work piece 2.

A beam splitter 17 is located between the dichroic mirror 16 and the beam-forming lens 9 in the radiation path of the processing laser radiation 8. This beam splitter 17 at the wavelength of the processing laser 8 transmits about 10%, while reflecting the remaining 90% of the processing laser radiation 8. Ideally, the beam splitter 17 transmits a portion as high as possible of the electromagnetic radiation 15 of the OCT unit 14.

The portion 8' of the processing laser radiation reflected back at the focus from or out of the workpiece 2, respectively, into the radiation path of the processing laser 7 is reflected by the beam splitter 17 onto a confocal detection unit 18 provided in addition to the imaging unit 14. The confocal detection unit 18 comprises a detector 19 such as a CCD-chip or a photomultiplier (PMT). A lens 20 focuses the processing laser radiation 8' reflected by the workpiece 2 to an aperture 21 which is disposed in front of the detector 19. Alternatively, a detector 19 with a very small detector surface can be used, which is placed directly in the focus of the lens 20, or the reflected radiation 8' can at the focus of the lens 20 be coupled into an optical fiber and directed via the optical fiber onto the detector 19.

The device 1 according to the invention further comprises a control unit 22. This control unit, which can for example be implemented in a PC, is connected via control and data lines 23 with the processing laser 7, the beam shaping unit composed of the beam shaping lens 9, and the deflection unit 10, the focusing lens 11, the OCT unit 14 and the confocal detector unit 18. Control commands can be transmitted via the control lines 23 from the control unit 22 to the processing laser 7 and the optical components in the radiation path of the laser radiation 8. Furthermore, measurement data and status data can be transmitted from these optical components as well as from the OCT unit 14 and the confocal detector unit 18 to the control unit 22. These data include, in particular, the z-position of the focusing lens 11. By adjustment in the z direction, i.e. along the optical axis of the processing laser radiation 8, the focusing lens 11 can change the depth of focus 12 in the interior of the workpiece 2. The dimensions x and y span a plane in the workpiece or the eye 2, respectively, perpendicular to the optical axis of the processing laser radiation 8.

Operation of the device 1 according to the invention or the method according to the invention is described below by way of example of laser treatment of a human eye lens 6.

First, a patient whose eye 2 is to be treated is placed on a bed and is driven with the movable bed into intersecting pilot laser beams or slit lamp images to a predetermined zero position. Subsequently, the imaging unit 14, i.e. in the present embodiment the OCT unit, monitors the eye 2 approaching the contact glass 13. The underside of the contact glass 13 and the front side of the eye 2 are visible in the OCT. During the approach towards the contact glass 13, the patient looks at a fixation light.

Once the cornea 3 of the eye 2 contacts the contact glass 13, the OCT unit 14 or the control unit 22 emits a respective signal to stop approaching. The patient continues to look into the fixation light, monitored through visual inspection by the physician, until the eye is fixed onto the curved contact glass 13 by a vacuum.

Once the workpiece 2 (in the present example, the eye) is fixed, the imaging unit 14 measures the workpiece 2. In the present example, the eye 2 is measured by the OCT unit 14 from the surface of the cornea 3 to the rear side of the eye lens 6. In particular, the apex 25 (i.e. the front center of the eye 2) of the cornea and/or the apex of the eye lens and/or four additional surface points 25' distributed around the apex 25 of the cornea or those of the eye lens are measured. In this manner, the imaging unit 14 obtains a high resolution image of the interior structures of the eye 2.

In the next step, the radiation 8 of the processing laser 7 is irradiated onto the eye 2. The average output power of the processing laser 7, however, is set to a value of 50% or less of the breakdown power. The breakdown power is that output at which the focus 12 of the laser radiation 8 achieves an optical breakdown in the workpiece 2. Using the deflection unit 10, the laser radiation 8 of the processing laser 7 is directed onto those surface points 23, 23' that have been previously measured with the imaging unit 14. The focusing lens 11 is adjusted in the z-direction so that the laser radiation 8 is focused in the z-direction at the apex 25 and/or the four other surface points 25' at different depths in the eye 2. The position of the focusing lens 11 in the z-direction is transmitted via the data line 23 to the control unit 22 and recorded there.

At each position of the focusing lens 11, measurement of the radiation 8' which is reflected back from the target volume is taken, i.e. the focus 12 of the processing laser 7, onto the confocal detection unit 18. The signal strength of the measured reflection is also provided via a data line 23 to the control unit 22. An evaluation unit 24 in the control unit 22 compares the sequence of the measurement signal from the confocal detector unit 18 with the respective position of the focusing lens 11 in the z-direction. At each boundary between two structures having different refractive indices in the eye 2, a peak of the measurement signal is detected by the confocal detector unit 18. Software can determine the peaks from the measurement signal using conventional algorithms. These peaks are correlated in the evaluation unit 24 with structures in the eye 2 determined by the imaging unit 14. In this manner, the coordinate system of the imaging unit 14 and the actual location of the focus 12 of the laser radiation 8 of the processing laser 7 are matched. This correlation or calibration is performed for a reference point in the interior of the workpiece 2, directly at or in the area later to be processed by the processing laser 7.

After calibration of the coordinate systems of the imaging unit 14 and the processing unit, in particular of the focusing lens 11, has been performed, the actual processing of the workpiece 2 can take place. For this purpose, the output of the processing laser 7 is raised to the breakdown output at which optical breakdowns are created at the focus 12 in the workpiece 2. During processing, the target area, i.e. the area processed in the workpiece 2, can be monitored using the imaging unit 14. In this manner, processing can be controlled and/or documented.

Based on the embodiment illustrated, the device 1 according to the invention and the method according to the invention can be modified in many ways. For example, the processing laser 7 does not need to be a femtosecond laser, but can also be a picosecond laser or an attosecond laser. It is also possible to match the coordinate systems of the imaging unit 14 and the processing laser 7 not in the eye lens 6 but on the iris 5, on or in the cornea to 3 or on the back of the eye. Areas or structures in the workpiece 2 which are perpendicular to the radiation path of the processing laser 7 are particularly suitable for calibration because a particularly high portion of the radiation 8' is reflected back onto the confocal detector unit 18.

The invention claimed is:

1. A device for processing material of a workpiece, comprising
    a processing laser configured for generating laser radiation in the form of short or ultrashort laser pulses,
    a focusing lens configured for focusing said laser radiation onto a focus in said workpiece,
    a beam deflection unit disposed between the processing laser and the workpiece for guiding said laser radiation such that the position of said focus of said laser radiation in said workpiece is three-dimensionally variable,
    a control unit configured for controlling said processing laser, said focusing lens and/or said beam deflection unit such that the location and/or extension of said focus of said laser radiation is variable,
    a detector unit configured for detecting said laser radiation being reflected or backscattered at said focus,
        wherein the intensity of said laser radiation at said focus is adjustable to a processing intensity, and to a measurement intensity which is lower than the processing intensity,
    wherein
    said detector unit is a confocal detector unit for confocal detection of said laser radiation which is reflected or backscattered at said focus,
        wherein an imaging unit using electromagnetic radiation for detecting structures within said workpiece is provided, where said electromagnetic radiation of said imaging unit is adapted to be irradiated into said workpiece via said beam deflection unit and said focusing lens,
        and wherein an evaluation unit is provided and adapted to compare the position of said focus of said laser radiation determined using said detector unit with the expected position of said focus in the image of said workpiece obtained by said imaging unit.

2. The device according to claim 1 wherein said electromagnetic radiation of said imaging unit differs in its wavelength from said laser radiation of said processing laser.

3. The device according to claim 1, wherein said imaging unit is an optical coherence tomography unit, OCT unit.

4. The device according to claim 1, wherein said control unit is configured to automatically correct the position of said focus of said laser radiation while considering a deviation of the determined position of said focus from the expected position of said focus.

5. The device according to claim 1, wherein a dichroic beam splitter is provided for coupling said electromagnetic radiation of said imaging unit in the radiation path of said laser radiation of said processing laser.

6. The device according to claim 1, wherein a beam splitter is provided for uncoupling said laser radiation to said detector unit, uncoupling at least 70% of said laser radiation to said detector unit.

7. The device according to claim 6, wherein the beam splitter uncouples 80% to 92% of said laser radiation.

8. The device according to claim 1, wherein said detector unit comprises an aperture, an optical fiber and/or a detector having a detector surface with a lateral dimension of the detector surface being 100 microns or less.

9. A method for calibrating a device for processing material of a workpiece, wherein said device comprises a processing laser for processing said workpiece and an imaging unit for monitoring and documenting the processing of material of said workpiece, said method comprising the steps of:
  a) focusing radiation of said processing laser with an intensity that is reduced in comparison to a processing intensity into different depths in the bulk of said workpiece below a surface point on said workpiece,
  b) detecting by a confocal detection the radiation reflected at said focus of said radiation of said processing laser,
  c) determining the depth of said focus at one or more peaks of said signal obtained during said detection in step b), said peaks generated by refractive index steps within the workpiece,
  d) calibrating said imaging unit for matching to the determined depth of said focus of said processing laser while considering the depth of said focus at said at least one peak of said signal obtained during said detection.

10. The method according to claim 9, wherein said steps a) to d) are performed at a plurality of surface points on said workpiece.

11. The method according to claim 9, wherein calibration of said imaging unit is performed dynamically in dependency on the respective location of said focus of said processing laser in said workpiece.

12. The method according to claim 9, wherein the position of said focus of said laser radiation is corrected while considering a deviation of the determined position of said focus from the expected position of said focus.

13. The method according to claim 9, wherein said imaging unit performs optical coherence tomography (OCT) of said workpiece.

* * * * *